United States Patent
Imai et al.

Patent Number: 5,849,318
Date of Patent: Dec. 15, 1998

[54] OIL-BASED SOLID COSMETIC COMPOSITION

[75] Inventors: Takeo Imai; Yuko Yago; Masashi Shibata, all of Tokyo, Japan

[73] Assignee: Kao Corporation, Tokyo, Japan

[21] Appl. No.: 872,050

[22] Filed: Jun. 10, 1997

[30] Foreign Application Priority Data

Jun. 26, 1996 [JP] Japan .................................. 8-165715

[51] Int. Cl.$^6$ .................................................. A61K 7/02
[52] U.S. Cl. ......................... 424/401; 424/78.03; 514/844
[58] Field of Search ................................ 424/401, 78.03

[56] References Cited

U.S. PATENT DOCUMENTS 4,792,444  12/1988  Fukasawa et al. ........................ 424/63

FOREIGN PATENT DOCUMENTS 4-89418  3/1992  Japan .
4-221306  8/1992  Japan .

*Primary Examiner*—Thurman K. Page
*Assistant Examiner*—James M. Spear
*Attorney, Agent, or Firm*—Oblon, Spivak, McClelland, Maier & Neustadt, P.C.

[57] ABSTRACT

Disclosed herein is an oil-based solid cosmetic composition comprising the following components (A) and (B): (A) 0.1–10 wt. % of a fluoroalkyl (meth)acrylate copolymer represented by the following general formula (1):

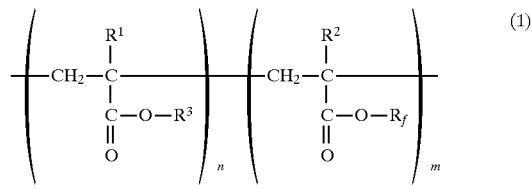

wherein $R^1$ and $R^2$ are independently a hydrogen atom or a methyl group, $R^3$ is a hydrocarbon group having 1–32 carbon atoms, $R_f$ is a group obtained by substituting part or the whole of hydrogen atoms of a hydrocarbon group having 1–32 carbon atoms with the corresponding number of fluorine atoms, and n and m are independently a number of 2–2,000 on the average; and (B) 2.9–50 wt. % of a solid oily substance having a melting point of 60°–120° C. The cosmetic composition is good in shape retention and a feeling upon use, has excellent gloss upon its application and can retain the good gloss and color after the application over a long period of time.

14 Claims, No Drawings

OIL-BASED SOLID COSMETIC COMPOSITION

BACKGROUND OF THE INVENTION

1. Field of the Invention

The present invention relates to an oil-based solid cosmetic composition which has excellent gloss upon its application, can retain the good gloss after the application over a long period of time, can last makeup longer and gives users a pleasant feeling upon use.

2. Description of the Background Art

The gloss of an oil-based solid cosmetic composition such as a lipstick or eye color stick upon use is important from the viewpoint of more enhanced makeup effect. It is a principal function required of such a makeup composition to retain its good finish over a long period of time. In order to enhance the gloss of the oil-based solid cosmetic compositions, oily substances such as castor oil, olive oil and lanolin derivatives have heretofore been used. However, those oil-based solid cosmetic compositions containing any of these oily substances have been accompanied by deteriorated feeling or shape retention upon use. It has therefore been attempted to add organopolysiloxane having a low polymerization degree or an oily substance extracted from a naturally occurring substance, thereby enhancing the gloss of the resulting oil-based solid cosmetic composition. However, its effect is not yet sufficient taking the retention of gloss after its application into consideration.

SUMMARY OF THE INVENTION

Accordingly, it is an object of the present invention to provide an oil-based solid cosmetic composition which is good in shape retention and a feeling upon use, has excellent gloss upon its application and can retain the good gloss after the application over a long period of time.

In view of the foregoing circumstances, the present inventors have carried out an extensive investigation. As a result, it has been found that when a small amount of a specific fluoroalkyl (meth)acrylate copolymer is used in combination with a solid oily substance, an oil-based solid cosmetic composition, which can satisfy the above-described performance characteristics, can be obtained even when any of the above-described oils is not used, thus leading to completion of the present invention.

According to the present invention, there is thus provided an oil-based solid cosmetic composition comprising the following components (A) and (B):

(A) 0.1–10 wt. % of a fluoroalkyl (meth)acrylate copolymer represented by the following general formula (1):

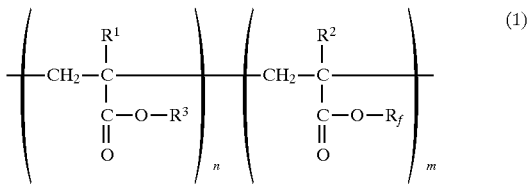

wherein $R^1$ and $R^2$ are independently a hydrogen atom or a methyl group, $R^3$ is a hydrocarbon group having 1–32 carbon atoms, $R_f$ is a group obtained by substituting part or the whole of hydrogen atoms of a hydrocarbon group having 1–32 carbon atoms with the corresponding number of fluorine atoms, and n and m are independently a number of 2–2,000 on the average; and (B) 2.9–50 wt. % of a solid oily substance having a melting point of 60°–120° C.

According to the present invention, the use of a small amount of the fluoroalkyl (meth)acrylate copolymer as the component (A) permits enhancing gloss upon application of the resulting oil-based solid cosmetic composition and moreover retention of the gloss without reducing the shape retention thereof. This effect is considered to be attributable to, for example, that the viscosity of the oil-based solid cosmetic composition upon its application is reduced due to enhancement of dispersibility of the solid oily substance.

The oil-based solid cosmetic composition according to the present invention has good shape retention and a feeling upon use and excellent gloss upon its application, and can retain the good gloss and color after the application over a long period of time. The oil-based solid composition according to the present invention is also useful in other fields, e.g. medicines and writing utensils such as crayons.

The above and other objects, features and advantages of the present invention will become apparent from the following description and the appended claims.

DETAILED DESCRIPTION OF THE PREFERRED EMBODIMENTS

The oil-based solid cosmetic composition as used herein means a cosmetic composition containing a relatively large amount of oily substances and having no fluidity at ordinary temperature (15°–25° C.) under ordinary pressure. No particular limitation is imposed on the shape thereof. However, examples of the shape include sticks, plates and those obtained by cast molding of the composition in dishes.

As cosmetic compositions in which a fluoroalkyl (meth)acrylate is incorporated, there have been known a cosmetic composition comprising a copolymer of a long-chain alkyl (meth)acrylate with a fluorinated alkyl group-containing (meth)acrylate as a film-forming component (Japanese Patent Application Laid-Open No. 289009/1986), an oil-based solid cosmetic composition comprising, as essential components, an oil-soluble polymeric substance containing the above copolymer, a volatile oily substance having a boiling point of 280° C. or lower and a solid fat having a penetration degree of 40 or lower (Japanese Patent Application Laid-Open No. 12710/1987 corresponding to EP-A-206671) and a solid cosmetic composition comprising a waxy fluorine-containing polymer, a volatile oily substance and an oil-gelling agent (Japanese Patent Application Laid-Open No. 221306/1992). However, all of these cosmetic compositions make use of the film-forming property of the fluoroalkyl (meth)acrylate copolymer, and are hence different from the cosmetic composition according to the present invention.

In the fluoroalkyl (meth)acrylate copolymer of the component (A) represented by the formula (1), $R^3$ is a hydrocarbon group having 1–32 carbon atoms. Of these, hydrocarbon groups having at least 8 carbon atoms are preferred in the present invention, with those having at least 12 carbon atoms being particularly preferred. Examples of such hydrocarbon groups include alkyl, phenyl, alkyl-substituted phenyl and alkenyl groups. Examples of the alkyl group include methyl, ethyl, n-propyl, isopropyl, n-butyl, sec-butyl, isobutyl, n-hexyl, n-heptyl, n-octyl, n-nonyl, n-decyl, n-undecyl, n-dodecyl, n-tetradecyl, n-hexadecyl, n-octadecyl, n-eicosyl and n-behenyl groups. Examples of the alkyl-substituted phenyl group include those obtained by substituting at least one hydrogen atom of a phenyl group with any of the above-described alkyl groups. Examples of the alkenyl group include vinyl, allyl, crotyl, α-pentenyl, 2-hexenyl, 3-methyl-2-butenyl, 1,1-dimethyl-2-propenyl and isoprenyl groups. As $R^3$, linear or branched alkyl groups having 8–32 carbon atoms are preferred, with linear or branched alkyl groups having 12–32 carbon atoms being particularly preferred.

$R_f$ is a group obtained by substituting part or the whole of hydrogen atoms of a hydrocarbon group having 1–32 carbon atoms, preferably 8–16 carbon atoms, with the corresponding number of fluorine atoms. Examples of such a hydrocarbon group include the same groups as those mentioned as $R^3$. Of these, linear or branched alkyl groups having 8–32 carbon atoms are preferred, with linear or branched alkyl groups having 8–16 carbon atoms being particularly preferred. Preferable examples of $R_f$ include $C_6F_{13}C_2H_4-$, $C_8F_{17}C_2H_4-$, $C_{10}F_{21}C_2H_4-$, $C_{11}F_{23}C_2H_4-$, $C_{12}F_{25}C_2H_4-$, $H(CF_2)_4C_2H_4-$, $H(CF_2)_5C_2H_4-$, $H(CF_2)_6C_2H_4-$ and $H(CF_2)_8C_2H_4-$. n and m are independently a number of 2–2,000 on the average. However, n is preferably a number of 2–1,000, while m is preferably a number of 2–100.

Examples of the fluoroalkyl (meth)acrylate copolymer (1) include copolymers of perfluorooctylethyl methacrylate with stearyl methacrylate, copolymers of perfluorodecylethyl methacrylate with myristyl methacrylate, copolymers of perfluorodecylethyl acrylate with stearyl methacrylate and copolymers of perfluoroundecylethyl methacrylate with behenyl methacrylate.

Such a fluoroalkyl (meth)acrylate copolymer (1) can be prepared in accordance with, for example, the process described in Japanese Patent Application Laid-Open No. 54410/1988. More specifically, the copolymer can be prepared by polymerizing each at least one of fluoroalkyl (meth)acrylates and alkyl (meth)acrylates at 60°–65° C. in the presence of a solvent such as n-hexane or toluene in a nitrogen atmosphere. Reaction conditions such as the molar ratio of the fluoroalkyl (meth)acrylate to the alkyl (meth) acrylate and the amount of a polymerization initiator can be selected, thereby obtaining a fluoroalkyl (meth)acrylate copolymer (1) containing these comonomers at a desired ratio. Precise sequence of the individual monomer units in the formula (1) is not particularly limited. Namely, the resulting copolymer may be a random or block copolymer.

The weight average molecular weight of the fluoroalkyl (meth)acrylate copolymer (1) is preferably 10,000–1,000,000, more preferably 10,000–500,000, most preferably 10,000–300,000. The weight average molecular weight mentioned above can be measured by Gel Permeation Chromatography (GPC) method using tetrahydrofuran (THF) as a solvent and polystyrene as a standard.

The fluoroalkyl (meth)acrylate copolymer (1) is incorporated in an amount of 0.1–10 wt. %, preferably 0.1–8 wt. %, more preferably 0.5–8 wt. %, based on the total weight of the oil-based solid cosmetic composition. It is particularly preferable to incorporate the copolymer in an amount of 1–5 wt. % from a practical point of view. If the amount of the copolymer to be incorporated is less than 0.1 wt. %, its effects of enhancing gloss and retaining such gloss cannot be sufficiently achieved. On the other hand, any amount exceeding 10 wt. % results in an oil-based solid cosmetic composition deteriorated in usability and a feeling upon use.

The solid oily substance of the component (B) has a melting point of 60°–120° C., preferably 65°–110° C. The melting points herein mentioned can be measured by known method., e.g. a capillary method. Any solid oily substance having a melting point lower than 60° C. is not preferred from the viewpoint of shape retention of the resulting composition because such a substance has poor solidifying ability. On the other hand, any solid oily substance having a melting point higher than 120° C. is also not preferred because such a substance requires a higher-temperature operation upon melting.

Such a solid oily substance may be either a natural substance or a synthetic substance. Examples thereof include vegetable waxes such as candelilla wax, carnauba wax, rice wax, Japan wax and jojoba oil; animal waxes such as bees wax and spermaceti; mineral waxes such as montan wax, ozokerite and ceresin; petroleum waxes such as paraffin wax and microcrystalline wax; synthetic hydrocarbon waxes such as polyolefin wax and Fischer-Tropsch wax; modified waxes such as montan wax derivatives, paraffin wax derivatives, microcrystalline wax derivatives and polyolefin wax derivatives; hydrogenated waxes such as hardened castor oil and hardened castor oil derivatives; various fatty acids and derivatives thereof, such as 12-hydroxystearic acid, stearic acid amide, phthalic anhydride imide and chlorinated hydrocarbons; and acid amides, esters and ketones.

Of these, paraffin wax, ozokerite, ceresin, polyolefin wax, candelilla wax and carnauba wax are preferred in the present invention.

In order to make the hardness of the oil-based solid cosmetic composition moderate to give users a pleasant feeling upon use and to achieve sufficient shape retention, an amount of the solid oily substance (B) to be incorporated is 2.9–50 wt. %, preferably 4.9–40 wt. %, more preferably 10–40 wt. %, based on the total weight of the oil-based solid cosmetic composition.

The amounts of the components (A) and (B) to be incorporated are selected from the above respective ranges according to the use application, form and the like of the cosmetic composition. A weight ratio of the component (A) to the component (B) is preferably 0.01–0.5, particularly 0.05–0.5.

In the oil-based solid cosmetic composition according to the present invention, other ingredients commonly used in the conventional oil-based solid cosmetic compositions may be suitably incorporated in addition to the above-described essential components so far as no detrimental influence is thereby imposed on the effects of the present invention. Those ingredients are, for example, oily substances, waxes other than those having a melting point of 60°–120° C., powders, dyes, polymer compounds other than the present component (A), perfume bases, surfactants, antioxidants, antiseptics and beautifying components. Besides, pigments commonly used in the conventional oil-based solid cosmetic compositions may be suitably incorporated in the oil-based solid cosmetic composition according to the present invention so far as no detrimental influence is thereby imposed on the effects of the present invention. As the pigments, there may be used known pigments generally employed in cosmetic compositions. Specific examples thereof include extender pigments such as talc, sericite, mica, kaolin, silica, nylon powder, polyethylene powder and cellulose powder; colorants such as carbon black, titanium oxide, iron oxide, zinc oxide, ultramarine blue, iron blue, chromium oxide, organic tar pigments and lakes; and combined pigments such as titanium mica and iron oxide-coated mica. These pigments for cosmetic compositions may be surface-treated with silicone, a higher fatty acid, a higher alcohol, a fatty acid ester, a metallic soap, an amino acid, an alkyl phosphate or the like, or encapsulated in organic or inorganic microcapsules before use.

The oil-based solid cosmetic composition according to the present invention comprises a small amount of the component (A) in combination with the solid oily substance component (B), whereby gloss upon its application is enhanced, retention of such gloss is also enhanced, and moreover a pleasant feeling upon use can be given to users. Therefore, the oil-based solid cosmetic composition according to the present invention is different from such conventional film-forming cosmetic composition containing the fluoroalkyl (meth)acrylate copolymer as described above. In addition, the oil-based solid cosmetic composition according to the present invention does substantially not require to incorporate any volatile oily substance, which has heretofore been used as a solvent for the fluoroalkyl (meth)acrylate copolymer. If the volatile oily substance is incorporated, its amount is at most 1 wt. % based on the total weight of the cosmetic composition.

Examples of the oil-based solid cosmetic composition according to the present invention include lipstick, lip cream, foundation, eye shadow, eyebrow and eyeliner. Of these, preferable are lipstick, lip cream, eyebrow, and eyeliner, particularly preferable are lipstick and lip cream.

The present invention will hereinafter be described in more detail by the following Synthesis Example, Test Examples, Examples and Comparative Examples. However, the present invention is not limited to or by these examples. Incidentally, all designations of "part" or "parts" as will be used in the examples mean part or parts by weight.

SYNTHESIS EXAMPLE 1

A 4-necked flask (300 ml) was charged with 20.0 g of perfluorooctylethyl methacrylate [$CH_2=C(CH_3)COOC_2H_4C_8F_{17}$], 30.0 g of stearyl methacrylate, 50 g of n-hexane and 0.32 g of 2,2'-azobis(2,4-dimethyl-valeronitrile) to prepare a solution under stirring. After purging with nitrogen, the monomers were polymerized for 5 hours at 60°–65° C. in a nitrogen atmosphere and further for 30 minutes under reflux. Ethanol as a precipitant was added to the resultant solution to precipitate a product formed. The product was then heated and dried under reduced pressure, thereby obtaining a fluoroalkyl methacrylate copolymer (Mw=81,000; m=144; n=72) containing perfluorooctylethyl methacrylate and stearyl methacrylate at a ratio of 4:6.

TEST EXAMPLE 1

After 20 parts of Polywax 655 (trade name; polyethylene wax having a melting point of 102° C.; product of Toyo Petrolite K.K.) and 80 parts of n-butyl myristate (product of Tokyo Kasei Kogyo Co., Ltd.) were heated and mixed, the resultant mixture was cooled and solidified to obtain a comparative product. After 20 parts of Polywax 655 (product of Toyo Petrolite K.K.), 79 parts of n-butyl myristate (product of Tokyo Kasei Kogyo Co., Ltd.) and 1 part of a fluoroalkyl methacrylate copolymer obtained in Synthesis Example 1 or produced in a manner similar to Synthesis Example 1 were heated and mixed, the resultant mixture was cooled and solidified to obtain invention products 1 to 3. The comparative product and invention products 1 to 3 were separately brayed on a glass plate by a spatula to measure their viscosities by a method using a rheometer (RFS-2 Model manufactured by Rheometrics Co.). Besides, their gloss was organoleptically evaluated by 10 expert panelists. The results are shown in Table 1.

TABLE 1

|  | Components incorporated | Viscosity (P) | Gloss |
|---|---|---|---|
| Comparative product | Polywax 655 20 parts<br>n-Butyl myristate 80 parts | 3,000 | Δ |
| Invention product 1 | Polywax 655 20 parts<br>n-Butyl myristate 79 parts<br>Fluoroalkyl (meth) acrylate copolymer[*1] (perfluorooctylethyl methacrylate:stearyl methacrylate = 3:7) 1 part | 450 | ⊚ |
| Invention product 2 | Polywax 655 20 parts<br>n-Butyl myristate 79 parts<br>Fluoroalkyl (meth) acrylate copolymer[*2] (perfluorooctylethyl methacrylate:stearyl methacrylate = 4:6) 1 part | 180 | ⊚ |
| Invention product 3 | Polywax 655 20 parts<br>n-Butyl myristate 79 parts<br>Fluoroalkyl (meth) acrylate copolymer[*3] (perfluorooctylethyl methacrylate:stearyl methacrylate = 5:5) 1 part | 150 | ⊚ |

⊚: Good; ○: Somewhat good; Δ: Fair; X: Poor.
[*1]Mw = 93,000, m = 192, n = 62;
[*2]Mw = 81,000, m = 144, n = 72;
[*3]Mw = 77,000, m = 114, n = 86.

EXAMPLES 1–4 AND COMPARATIVE EXAMPLES 1–3

Lipsticks were prepared in accordance with their corresponding compositions shown in Table 2.

TABLE 2

| | wt. % | | | | | |
|---|---|---|---|---|---|---|
| Components incorporated | Example 1 | Example 2 | Example 3 | Comp. Ex. 1 | Comp. Ex. 2 | Comp. Ex. 3 |
| Fluoroalkyl (meth)acrylate copolymer[*4] (perfluorooctylethyl methacrylate:stearyl methacrylate = 4:6) | 3.0 | | | | 3.0 | 3.0 |
| Fluoroalkyl (meth)acrylate copolymer[*5] (perfluorooctylethyl methacrylate:stearyl methacrylate = 3:7) | | 3.0 | | | | |
| Fluoroalkyl (meth)acrylate copolymer[*6] (perfluorooctylethyl methacrylate:stearyl methacrylate = 5:5) | | | 3.0 | | | |
| Castor oil | 10.0 | 10.0 | 10.0 | 10.0 | | |
| Solid paraffin (melting point: 70° C.) | 10.0 | 10.0 | 10.0 | 10.0 | | |
| Candelilla wax (melting point: 69° C.) | 4.0 | 4.0 | 4.0 | 4.0 | | |
| Carnauba wax (melting point: 83° C.) | 3.0 | 3.0 | 3.0 | 3.0 | | |

TABLE 2-continued

| | wt. % | | | | | |
|---|---|---|---|---|---|---|
| Components incorporated | Example 1 | Example 2 | Example 3 | Comp. Ex. 1 | Comp. Ex. 2 | Comp. Ex. 3 |
| Liquid paraffin | 40.0 | 40.0 | 40.0 | 43.0 | 50.0 | 50.0 |
| Triglyceryl isostearate | 23.0 | 23.0 | 23.0 | 23.0 | | |
| Red Color No. 201 | 2.0 | 2.0 | 2.0 | 2.0 | | |
| Red Color No. 202 | 1.0 | 1.0 | 1.0 | 1.0 | | |
| Red Color No. 104(1) | 2.0 | 2.0 | 2.0 | 2.0 | | |
| Titanium oxide | 2.0 | 2.0 | 2.0 | 2.0 | | |
| Polyethylene wax (melting point: 125° C.) | | | | | 17.0 | |
| Solid paraffin (melting point: 55° C.) | | | | | | 35.0 |

*4: Mw = 80,000, m = 122, n = 71;
*5: Mw = 95,000, m = 202, n = 85;
*6: Mw = 77,000, m = 114, n = 86.

(Preparation process)

Base materials were heated and melted, and were then mixed uniformly. Color materials were added to the melt. After kneading the resultant mixture and dispersing the color materials evenly by a roll mill, the mixture was melted again. The melt was defoamed and then cast into a mold.

TEST EXAMPLE 2

Ten expert panelists were got to use the lipsticks obtained in Example 1 and Comparative Example 1, thereby organoleptically evaluating them as to a feeling upon use. The results are shown in Table 3.

TABLE 3

| | Ex. 1 | Ex. 2 | Ex. 3 | Comp. Ex. 1 | Comp. Ex. 2 | Comp. Ex. 3 |
|---|---|---|---|---|---|---|
| Spreadability upon application | ⊙ | ⊙ | ⊙ | ○ | Δ | X |
| Conformability | ○ | ○ | ○ | ○ | Δ | Δ |
| Gloss right after application | ⊙ | ⊙ | ⊙ | Δ | ○ | ○ |
| Moistured feeling upon application | ⊙ | ○ | ⊙ | Δ | Δ | X |
| Shape retention | ○ | ⊙ | ○ | ○ | ○ | Δ |
| Retention of gloss | ⊙ | ⊙ | ⊙ | Δ | Δ | Δ |
| Retention of moistured feeling | ○ | Δ | ○ | X | X | X |

⊙: Good; ○: Somewhat good; Δ: Fair; X: Poor.

EXAMPLE 4 AND COMPARATIVE EXAMPLE 4

Eye brow compositions were prepared in accordance with their corresponding formulations shown in Table 4.

TABLE 4

| | wt. % | |
|---|---|---|
| Components incorporated | Example 4 | Comparative Example 4 |
| Fluoroalkyl (meth)acrylate copolymer*7 (perfluoroundecylethyl methacrylate: behenyl methacrylate = 1:1) | 3.0 | |
| Ceresin (melting point: 81° C.) | 3.0 | 6.0 |
| Paraffin wax (melting point: 68° C.) | 24.0 | 24.0 |
| Bees wax (melting point: 65° C.) | 5.0 | 5.0 |
| Vaseline | 7.0 | 7.0 |
| Lanolin (melting point: 50° C.) | 5.0 | 5.0 |
| Liquid paraffin | 7.0 | 7.0 |

TABLE 4-continued

| | wt. % | |
|---|---|---|
| Components incorporated | Example 4 | Comparative Example 4 |
| Isopropyl myristate | 4.0 | 4.0 |
| Pigment | 29.0 | 29.0 |

*7 Mw = 108,000, m = 137, n = 83.

(Preparation process)

Raw materials other than a pigment were heated and melted, and were then mixed uniformly. The pigment was added to the melt. After thoroughly stirring and kneading the resultant mixture and dispersing the pigment evenly by a roll mill, the mixture was cooled and crushed, followed by extrusion through a nozzle having an inner diameter of 3 mm.

TEST EXAMPLE 3

Ten expert panelists were got to use the eye brow compositions obtained in Example 4 and Comparative Example 4, thereby organoleptically evaluating them as to gloss and a feeling upon use. The results are shown in Table 5.

TABLE 5

| | Example 4 | Comparative Example 4 |
|---|---|---|
| Gloss right after application | ○ | Δ |
| Gloss after 1 hour from application | ○ | X |
| Feeling upon use | ⊙ | Δ |

⊙: Good; ○: Somewhat good; Δ: Fair; X: Poor.

What is claimed is:

1. An oil-based solid cosmetic composition comprising the following components (A) and (B):

(A) 0.1–10 wt. % of a fluoroalkyl (meth)acrylate copolymer represented by the following general formula (1):

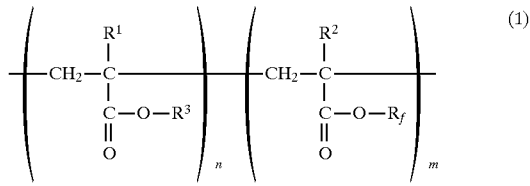

wherein $R^1$ and $R^2$ are independently a hydrogen atom or a methyl group, $R^3$ is a hydrocarbon group having 1–32 carbon atoms, $R_f$ is a group obtained by substituting part or the whole of hydrogen atoms of a hydrocarbon group having 1–32 carbon atoms with the corresponding number of fluorine atoms, and n and m are independently a number of 2–2,000 on the average; and (B) 2.9–50 wt. % of a solid oily substance having a melting point of 60°–120° C., wherein said cosmetic composition comprises 0 to less than 1% volatile oil.

2. The oil-based solid cosmetic composition according to claim 1, wherein the weight average molecular weight of the fluoroalkyl (meth)acrylate copolymer of the component (A) is 10,000–1,000,000.

3. The oil-based solid cosmetic composition according to claim 1 or 2, wherein the component (A) is contained in an amount of 0.1–8 wt. % based on the total weight of the composition.

4. The oil-based solid cosmetic composition according to any one of claims 1 to 2, wherein the component (B) is contained in an amount of 4.9–40 wt. % based on the total weight of the composition.

5. The oil-based solid cosmetic composition according to any one of claims 1 to 2, wherein the composition substantially contains no volatile oily substance.

6. The oil-based solid cosmetic composition according to claim 3, wherein the component (B) is contained in an amount of 4.9–40 wt. % based on the total weight of the composition.

7. The oil-based solid cosmetic composition according to claim 3, wherein the composition substantially contains no volatile oily substance.

8. The oil-based solid cosmetic composition according to claim 4, wherein the composition substantially contains no volatile oily substance.

9. The oil-based solid cosmetic composition according to claim 1, wherein said cosmetic composition comprises 0 to 0.5% volatile oil.

10. The oil-based solid cosmetic composition according to claim 2, wherein said cosmetic composition comprises 0 to 0.5% volatile oil.

11. The oil-based solid cosmetic composition according to claim 1, wherein said composition comprises 1–5% of said fluoroalkyl (meth)acrylate copolymer.

12. The oil-based solid cosmetic composition according to claim 1, comprising 10–40 wt. % of said solid oily substance.

13. The oil-based solid cosmetic composition according to claim 1, wherein a weight ratio of said fluoroalkyl (meth)acrylate copolymer to said solid oily substance is 0.05–0.5.

14. The oil-based solid cosmetic composition according to claim 10, comprising 1–5% of said fluoroalkyl (meth)acrylate copolymer, 10–40 wt. % of said solid oily substance, and wherein a weight ratio of said fluoroalkyl (meth)acrylate copolymer to said solid oily substance is 0.05–0.5.

* * * * *